US012765810B2

(12) United States Patent
Yang

(10) Patent No.: US 12,765,810 B2
(45) Date of Patent: Oct. 20, 2026

(54) HIGHLY INTEGRATED ANALYTE DETECTION DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 338 days.

(21) Appl. No.: 18/562,842

(22) PCT Filed: Dec. 8, 2021

(86) PCT No.: PCT/CN2021/136533
§ 371 (c)(1),
(2) Date: Nov. 21, 2023

(87) PCT Pub. No.: WO2022/252550
PCT Pub. Date: Dec. 8, 2022

(65) Prior Publication Data
US 2024/0237926 A1 Jul. 18, 2024

(30) Foreign Application Priority Data
May 31, 2021 (WO) ................ PCT/CN2021/097188

(51) Int. Cl.
*A61B 5/145* (2006.01)
*A61B 5/00* (2006.01)
(Continued)

(52) U.S. Cl.
CPC .......... *A61B 5/14546* (2013.01); *A61B 5/002* (2013.01); *A61B 5/14865* (2013.01);
(Continued)

(58) Field of Classification Search
CPC .... A61B 5/145; A61B 5/14532; H01M 50/10; H01M 50/148; H01M 50/167; H01M 50/102
See application file for complete search history.

(56) References Cited

U.S. PATENT DOCUMENTS

2009/0030294 A1 1/2009 Petisce et al.
2015/0207181 A1* 7/2015 Fink .................... H01M 10/425 429/7
(Continued)

FOREIGN PATENT DOCUMENTS

CN 102569680 A * 7/2012
CN 106470593 3/2017
(Continued)

OTHER PUBLICATIONS

"International Search Report (Form PCT/ISA/210) of PCT/CN2021/136533", mailed on Mar. 1, 2022, pp. 1-2.

*Primary Examiner* — Sean P Dougherty
(74) *Attorney, Agent, or Firm* — JCIP GLOBAL INC.

(57) ABSTRACT

A highly integrated analyte detection device is provided. The device includes a bottom case used for mounting on the surface of human skin; a sensor assembled on the bottom case for detecting analyte parameter information in the user's body; a transmitter module including a shell, a circuit board, a transmitter and an electrical contact, the electrical contact electrically connected with the sensor, the transmitter used to transmit the analyte parameter information to external equipment; and a battery cavity located within the transmitter module. The battery cavity includes a cavity shell, a diaphragm, electrolyte, an anode plate, a cathode plate and a conductive strip. The cavity shell includes an upper cover shell and a lower shell, the upper cover shell is integrated with the circuit board.

13 Claims, 9 Drawing Sheets

(51) Int. Cl.

| | |
|---|---|
| ***A61B 5/1486*** | (2006.01) |
| ***H01M 50/10*** | (2021.01) |
| ***H01M 50/124*** | (2021.01) |
| ***H01M 50/148*** | (2021.01) |
| ***H01M 50/167*** | (2021.01) |
| ***H01M 50/169*** | (2021.01) |
| ***H01M 50/186*** | (2021.01) |

(52) U.S. Cl.

CPC ..... *H01M 50/1243* (2021.01); *H01M 50/186* (2021.01); *A61B 5/145* (2013.01); *A61B 5/14532* (2013.01); *A61B 2560/0214* (2013.01); *A61B 2560/045* (2013.01); *A61B 2560/0462* (2013.01); *A61B 2562/16* (2013.01); *A61B 2562/227* (2013.01); *H01M 50/10* (2021.01); *H01M 50/148* (2021.01); *H01M 50/167* (2021.01); *H01M 50/169* (2021.01)

(56) References Cited

U.S. PATENT DOCUMENTS

| | | | | |
|---|---|---|---|---|
| 2017/0290512 | A1* | 10/2017 | Antonio ................ | A61M 5/158 |
| 2017/0290546 | A1* | 10/2017 | Antonio ............. | A61B 5/14865 |
| 2018/0309168 | A1* | 10/2018 | Liao .................. | H01M 10/0567 |

FOREIGN PATENT DOCUMENTS

| | | |
|---|---|---|
| CN | 107361775 | 11/2017 |
| CN | 109998555 | 7/2019 |
| CN | 109998560 | 7/2019 |
| CN | 113274006 | 8/2021 |

* cited by examiner

HIGHLY INTEGRATED ANALYTE DETECTION DEVICE

CROSS-REFERENCE TO RELATED APPLICATION

This application is a 371 of international application of PCT application serial no. PCT/CN2021/136533, filed on Dec. 8, 2021, which claims the priority benefit of PCT application no. PCT/CN2021/097188, filed on May 31, 2021. The entirety of each of the above mentioned patent applications is hereby incorporated by reference herein and made a part of this specification.

TECHNICAL FIELD

The invention mainly relates to the field of medical devices, in particular to a highly integrated analyte detection device.

BACKGROUND

The pancreas in the normal human body automatically monitors the glucose level in the blood and secretes the required insulin/glucagon automatically. In diabetics, however, the pancreas does not function properly and cannot properly produce the insulin the body needs. Therefore, diabetes is a metabolic disease caused by abnormal pancreas function, and diabetes is a lifelong disease. At present, the medical technology cannot cure diabetes completely, but can only control the occurrence and development of diabetes and its complications by stabilizing blood glucose.

Diabetics need to test their blood glucose before injecting insulin into the body. Most of the current methods can continuously monitor blood glucose and send data to a remote device in real time for users to view. This method is called Continuous Glucose Monitoring (CGM). This method requires the detection device to be attached to the skin surface, and the probe carried by it is inserted into the subcutaneous tissue fluid to complete the detection.

Existing technology of analyte detection devices, power is supplied by button battery and thus the analyte detection device is subject to button battery in the shape and size, increased the difficulty of the device further miniaturization design, secondly, button battery storage capacity is limited, can't meet the job requirements of the analyte detection device for a long time.

Therefore, the existing technology is in urgent need of a highly integrated analyte detection device with smaller battery volume and larger capacity.

BRIEF SUMMARY OF THE INVENTION

The embodiment of the invention discloses a highly integrated analyte detection device, a battery cavity is arranged in the transmitter module, the cavity shell is integrated with the shell of the transmitter module and circuit board. The diaphragm, the electrolyte, the anode plate, the cathode plate and the pole ear are arranged in the cavity shell, the electrolyte insulation layer is also arranged in the cavity shell, to form the highly integrated analyte detection device with battery, shell of transmitter module and circuit board integration, the shape and size of the analyte detection device are no longer limited by the shape and size of the button battery. After the integration of the battery, shell of transmitter module and circuit board, the battery has more available space and smaller occupied volume, which can meet the design requirements of analyte detection device miniaturization.

The invention discloses a highly integrated analyte detection device, which comprises a bottom case, the bottom case is installed on the surface of human skin; The sensor is assembled on the bottom case to detect the parameter information of analyte in the user's body; The transmitter module comprises a shell, a circuit board, a transmitter and an electrical contact, the electrical contact is electrically connected with the sensor, the transmitter is used to transmit the analyte parameter information to external equipment; And the battery cavity is located within the transmitter module, the battery cavity comprises the cavity shell, diaphragm, electrolyte, anode plate, cathode plate and conductive strip, the cavity shell comprises an upper cover shell and a lower shell, the upper cover shell is integrated with the circuit board.

According to one aspect of the invention, the lower shell is integrated with the shell of transmitter module.

According to one aspect of the invention, the electrolyte insulation layer is arranged in the cavity shell.

According to one aspect of the invention, the electrolyte insulation layer is made of TPE or PET material.

According to one aspect of the invention, the electrolyte isolation layer is a film arranged on the inner wall of the cavity shell.

According to one aspect of the invention, the thickness of the film is 300-500 um.

According to one aspect of the invention, the electrolyte isolation layer is a closed shell independent of the cavity shell.

According to one aspect of the invention, the cavity shell material is PE, PP, HDPE, PVC, ABS, PMMA, PC, PPS or PU.

According to one aspect of the invention, the sealant is coated at the junction of the upper cover shell and the lower shell.

According to one aspect of the invention, the sealant is one of hot melt adhesive and silica gel.

According to one aspect of the invention, the anode plate and the cathode plate are electrically connected to the circuit board through the conductive strip.

According to one aspect of the invention, the conductive strip is fixedly connected to the circuit board by solder or solder paste.

According to one aspect of the invention, the analyte detection device also comprises the connector, which comprises at least two conductive zones and an insulating zone arranged alternately for using as the electrical connection medium for the electrical contact and sensor.

Compared with the prior art, the technical scheme of the invention has the following advantages: The invention discloses a highly integrated analyte detection device, the transmitter module is provided with the battery cavity, the battery cavity comprises cavity shell, diaphragm, electrolyte, the anode plate, cathode plate and conductive strip, the electrolyte isolation layer is also arranged inside the cavity shell, to form the structure of battery, shell of transmitter and circuit board integration, the shape and size of the analyte detection device are no longer limited by the shape and size of the shell of button battery, and the shape and size of the battery cavity can be optimized according to the miniaturization design requirements of the analyte detection device to improve user experience.

Further, the structure design of battery, shell of transmitter and circuit board integration, which can make full use of space of detection device. When the volume of analyte detection device becomes smaller, more active substances can be filled in the battery cavity, therefore, compared with the button battery, the battery cavity power increases, and the endurance time of analyte detection device is increased.

Further, the lower shell of the battery cavity is integrated with the shell of transmitter, and the upper cover shell of the battery cavity is integrated with the circuit board. A good sealing environment is formed in the cavity shell, which can prevent electrolyte leakage and external air and water from entering the cavity shell.

Further, the electrolyte insulation layer is made of TPE or PET material, which can effectively prevent corrosion of the cavity shell caused by the electrolyte.

DETAILED DESCRIPTION

As mentioned above, the shape and size of existing analyte detection devices are limited by the shape and size of button battery shell, which increases the difficulty of further miniaturization design of device.

In order to solve the problem, the invention provides a highly integrated analyte detection device. The transmitter module is provided with a battery cavity, which comprises the cavity shell, the diaphragm, the electrolyte, the anode plate, the cathode plate and the conductive strip. The electrolyte insulation layer is also provided inside the cavity shell, forming an integrated structure of battery, shell of transmitter and circuit board. The shape and size of the analyte detection device are no longer limited by the shape and size of the button battery shell, and the shape and size of the battery cavity can be optimized according to the miniaturization design requirements of the analyte detection device to improve user experience.

Various exemplary embodiments of the invention will now be described in detail with reference to the attached drawings. It is understood that, unless otherwise specified, the relative arrangement of parts and steps, numerical expressions and values described in these embodiments shall not be construed as limitations on the scope of the present invention.

In addition, it should be understood that the dimensions of the various components shown in the attached drawings are not necessarily drawn to actual proportions for ease of description, e.g. the thickness, width, length or distance of some elements may be enlarged relative to other structures.

The following descriptions of exemplary embodiments are illustrative only and do not in any sense limit the invention, its application or use. Techniques, methods and devices known to ordinary technicians in the relevant field may not be discussed in detail here, but to the extent applicable, they shall be considered as part of this manual.

It should be noted that similar labels and letters indicate similar items in the appending drawings below, so that once an item is defined or described in one of the appending drawings, there is no need to discuss it further in the subsequent appending drawings.

First Embodiment

Figure 1:
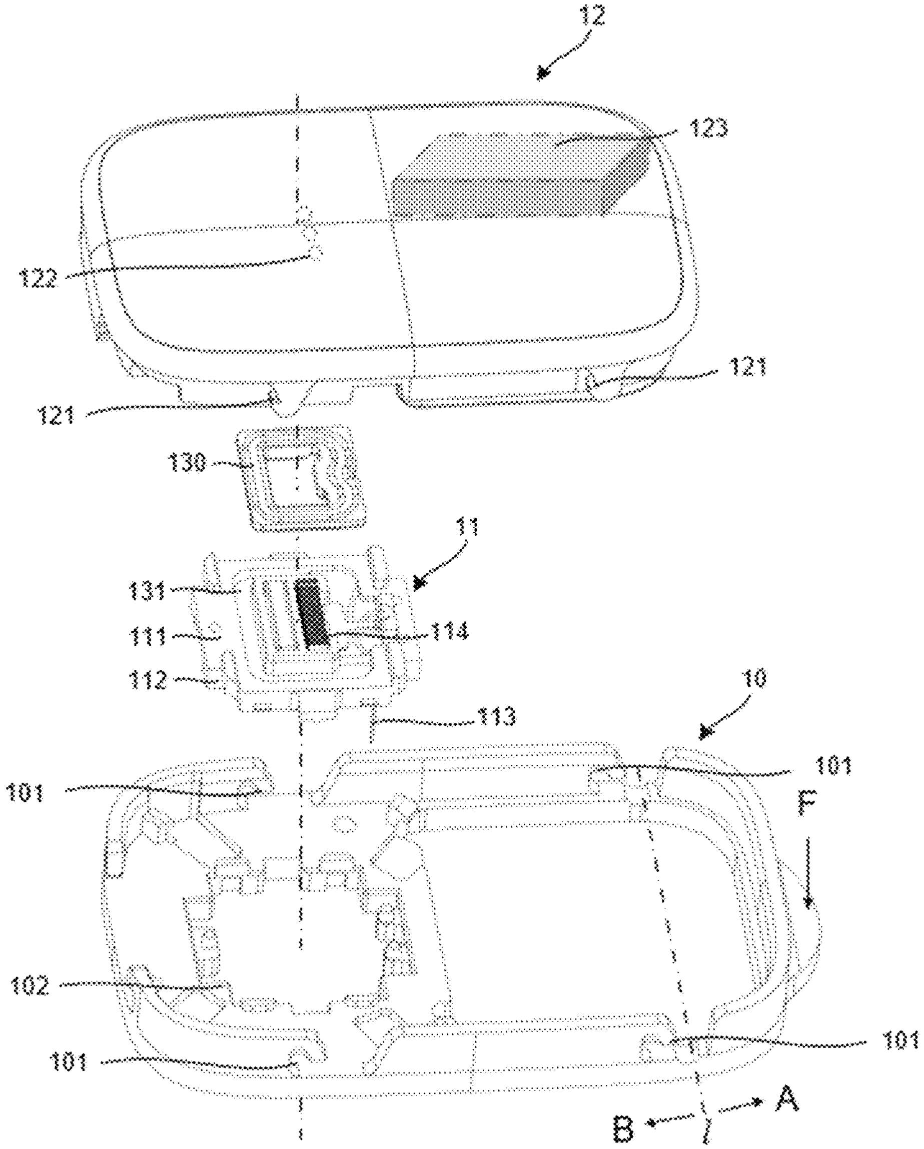
FIG. 1 is the schematic diagram of a highly integrated analyte detection device according to the first embodiment of the invention.

FIG. 1 is a schematic diagram of a highly integrated analyte detection device according to the first embodiment of the invention.

The detection device comprises the bottom case 10, the sensor 11, the transmitter 12 and the battery cavity 123.

The bottom case 10 is used to assemble transmitter 12 and sensor 11, and the detection device is glued to the skin surface through the bottom adhesive tape (not shown in the figure). Bottom case 10 comprises a fixing part and a force application part. The bottom case 10 is provided with at least one second clamping part 101. The second clamping part 101 is used for clamping the transmitter 12. Specifically, in an embodiment of the invention, the number of the second clamping part 101 is two. The two second clamping parts 101 correspond to the side walls of the bottom case 10.

Here, the fixing part and the force application part are relative concepts. Depending on the structural design of the bottom case 10 and the transmitter 12, the location of the fixing part and the force application part can be selected differently, which will be described in detail below.

Transmitter 12 is provided with at least one first clamping part 121. The first clamping part 121 corresponds to the second clamping part 101. The transmitter 12 is mounted on the bottom case 10 by clamping the second clamping part 101 and the first clamping part 121. Obviously, in an embodiment of the present invention, the transmitter 12 is provided with two first clamping parts 121, that is, two pairs of first clamping parts 121 and second clamping parts 101.

Here, the first clamping part 121 corresponds to the second clamping part 101, which means they have the same number and corresponding positions.

When separating bottom case 10 and transmitter 12, the fixing part is fixed by finger or other equipment, using another finger or other auxiliary equipment in one direction to apply force on the force application part, bottom case 10 will fail, the second clamping part 101 and the first clamping part 121 are separated from each other, and then the transmitter 12 and bottom case 10 are separated. That is, when separating bottom case 10 and transmitter 12, the user only applies force on the force application part in one direction with one finger to separate the two, which is convenient for the user to operate. After separation, the transmitter can be reused, reducing the cost to the user.

It should be noted here that failure is a common concept in the field of engineering materials. After failure, the material loses its original function and the failure part cannot be restored again. Since the second clamping part 101 is part of the bottom case 10, the failure of bottom case 10 comprises the failure of bottom plate, side wall or second clamping part 101 of bottom case 10. Therefore, the failure modes of bottom case 10 include bottom or side wall fracture of bottom case 10, bottom case 10 damage, second clamping part 101 fracture, and one or more of bottom case 10 plastic deformation. Obviously, after the failure of the base case 10, the base case 10 loses the function and function of clamping transmitter 12.

The way of fixing the fixing part comprises clamping, supporting and other ways. There are no specific restrictions here, as long as the conditions for fixing the fixing part can be met.

Figure 2:
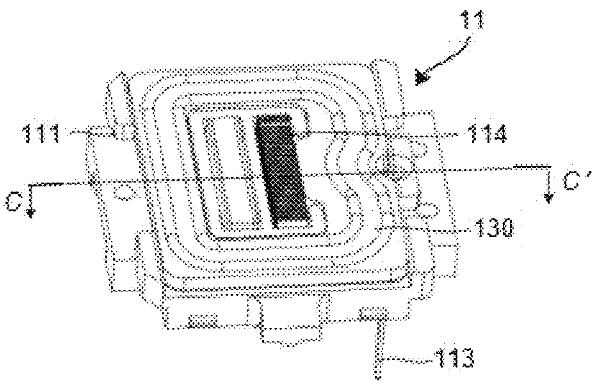
FIG. 2 is the schematic diagram of the three-dimensional structure of the sensor according to the first embodiment of the invention.

Combined with the schematic diagram of the three-dimensional structure of the sensor shown in FIG. 2, sensor 11 is installed on the bottom case 10, comprising at least probe 113 and connector 114. The probe 113 is used to pierce into human skin to detect the parameters of body fluid analyte and convert them into electrical signals, which are transmitted to the electrical contact 122 of transmitter 12 through connector 114. Transmitter 12 then transmits analyte parameter information to the user.

In an embodiment of the invention, the connector 114 comprises at least two conductive and insulating zones. Conductive zone and insulating zone play the role of electrical conduction and electrical insulation respectively. The conductive zone and the insulating zone can't be separated from each other, that is, the conductive zone and the insulating zone respectively belong to the whole part of the connector 114. Connector 114 can conduct electricity only longitudinally through the conductive zone, which insulates the conductive zones from each other and therefore cannot conduct electricity horizontally. A connector 114 plays the role of electrical conductivity and electrical insulation at the same time, the complexity of the internal structure of the detection device is reduced, the internal structure is more compact, and the integration of the detection device is improved.

Figure 3:
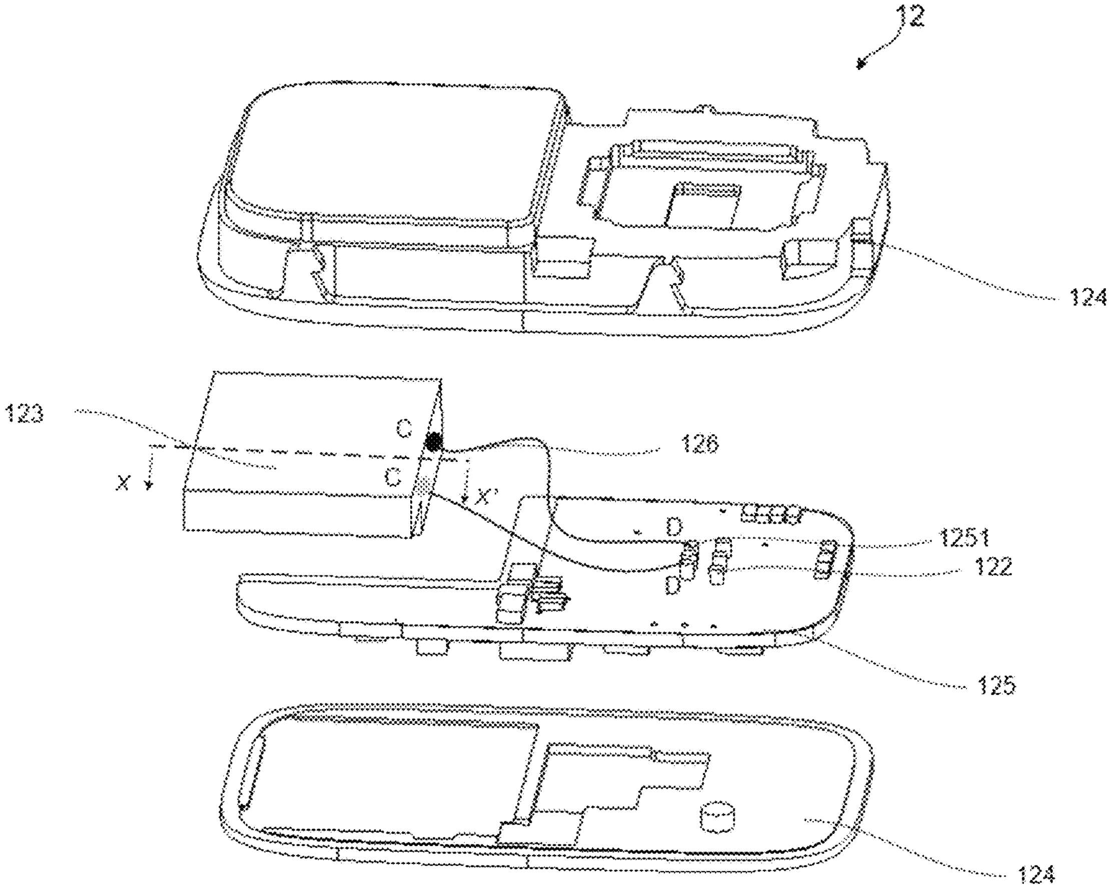
FIG. 3 is the internal structure of the transmitter according to the first embodiment of the invention.
Figure 4:
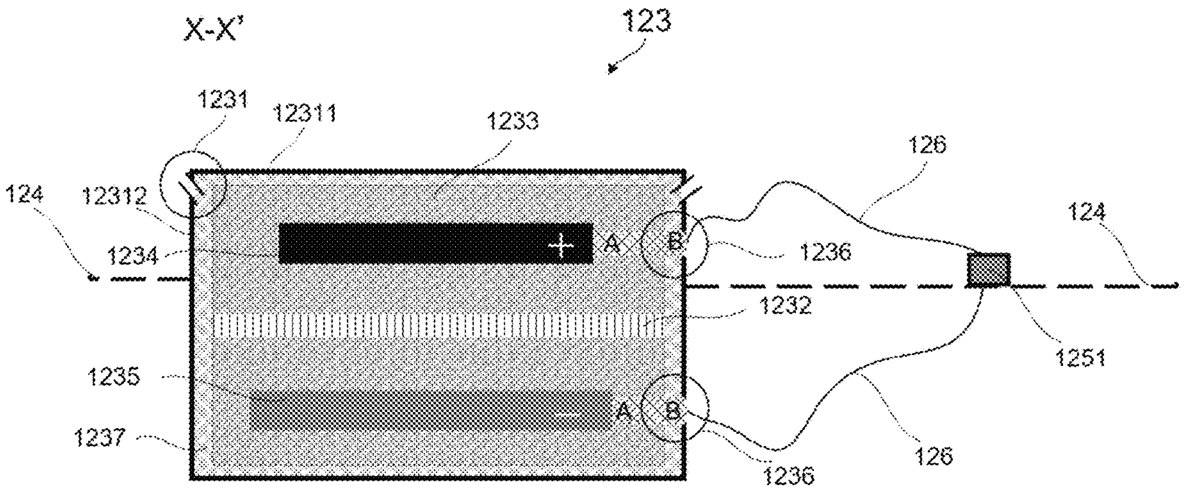
FIG. 4 is the schematic diagram of the X-X' section structure of the battery cavity according to the first embodiment of the invention.

FIG. 3 is an internal structure diagram of an embodiments transmitter according to the invention; FIG. 4 is a schematic diagram of the X-X' section structure of the battery cavity.

In combination with FIG. 3 and FIG. 4, in the embodiment of the present invention, battery cavity 123 is located in transmitter 12, and the lower shell 12312 of battery cavity shell 1231 is the shell 124 of the transmitter 12, so as to form a good seal and prevent electrolyte leakage, external air, water droplets and other debris from entering battery cavity 123. In the embodiment of the invention, the battery cavity 123 is electrically connected to the power electrode 1251 of the internal circuit 125 through wire 126 to supply power to the internal circuit 125.

The battery cavity 123 comprises the cavity shell 1231, the diaphragm 1232, the electrolyte 1233, the anode plate 1234, the cathode plate 1235 and pole ear 1236. The actual size and proportion of each part are not necessarily equal to the size and proportion of each part in FIG. 4.

In the embodiment of the invention, the cavity shell 1231 is made of one of PE, PP, HDPE, PVC, ABS, PMMA, PC, PPS or PU. Compared with the button battery with metal shell, the weight of the battery cavity 123 made of plastic shell 1231 can be greatly reduced, thus reducing the overall weight of the analyte detection device. Improved user experience. In the preferred embodiment of the invention, the cavity shell 1231 is divided into the upper cover shell 12311 and the lower shell 12312. The material of the lower shell 12312 is consistent with that of the transmitter shell 124, which is convenient for integrated injection molding during processing and improves production efficiency.

In an embodiment of the invention, the upper cover shell 12311 is closed to the lower shell 12312, and a closed chamber space is formed inside, and sealant is coated at the connection between the upper cover shell 12311 and the lower shell 12312.

In an embodiment of the invention, the cavity shell 1231 made of plastic material, such as PE (polyethylene), PP (polypropylene) and PC (polycarbonate), is easy to be corroded by the electrolyte, so an electrolyte insulation layer 1237 needs to be arranged inside the cavity shell 1231.

In an embodiment of the present invention, the section shape of cavity shell 1231 is not limited to the rectangle shown in the FIG., but can also be round, oval, triangular or other irregular shapes, and its three-dimensional structure can make full use of the available space between transmitter 12 and bottom case 10 to adapt to the miniaturization design of analyte detection device.

In an embodiment of the invention, the electrolyte insulation layer 1237 can be TPE or PET (polyethylene terephthalate), TPE is a thermoplastic elastomer material with strong processing ability, PET itself as the container of the electrolyte, can effectively isolate the corrosion of the electrolyte to the cavity shell and circuit devices.

In embodiments of the invention, the electrolyte insulation layer 1237 may be either a thin film coated inside the cavity shell 1231 by deposition or solution or a separate shell.

In the preferred embodiment of the invention, the electrolyte insulation layer 1237 is a film of 300-500 um thickness. If the electrolyte isolation layer 1237 is too thin, the membrane will be infiltrated and softened by the electrolyte, which will lead to aging of the membrane after a long time. If the electrolyte isolation layer 1237 is too thick, will occupy the space of the battery cavity. In a preferred embodiment of the invention, the thickness of the electrolyte insulation layer 1237 is 400 um.

In an embodiment of the invention, the solute of electrolyte 1233 is lithium salt, such as one of lithium perchlorate ($LiClO_4$), lithium hexafluorophosphate ($LiPF_6$), lithium tetrafluoroborate ($LiBF_4$). The solvent is one of vinyl carbonate, propylene carbonate, diethyl carbonate, dimethyl carbonate, methyl carbonate, phosphorus pentafluoride, hydrofluoric acid, ether, ethylene carbonate, propylene carbonate, diethyl carbonate. In the preferred embodiment of the invention, the solvent is organic solvent, such as ether, ethylene carbonate, propylene carbonate, diethyl carbonate.

In an embodiment of the invention, the main material of the anode plate 1234 is manganese dioxide and is prepared by the following process:

(1) The electrolytic manganese dioxide, conductive agent and binder were screened through a screen or air classifier, select the particle size less than 200 um electrolytic manganese dioxide particles, placed in the quartz boat, heat treatment was carried out in the sintering furnace and the temperature was heated to 200° C. for 4 h. The purpose of this step is to make electrolytic manganese dioxide lose part of binding water, X-ray diffraction peak shift, crystal plane spacing decrease, Mn—O bond force increase, so as to enhance the discharge capacity of electrolytic manganese dioxide.

(2) After the electrolytic manganese dioxide in step (1) is cooled to below 60° C., an electronic balance is used to weigh 9 g electrolytic manganese dioxide, 0.5 g conductive agent with particle size less than 200 um, and 0.5 g binder with particle size less than 200 um, put them in the grinding dish, fully stir and mix, then grind manually or electrically to get 10 g grinding mixture. And allows the grinding mixture to pass through a screen of 300 mesh (size 48 um). The purpose of this step is to ensure the uniformity of the mixture and avoid the phenomenon of uneven dispersion of conductive agent and binder.

In other embodiments of the invention, the mass proportion of electrolytic manganese dioxide, conductive agent and binder is not limited to the above proportion, and the mass proportion can be 80%-96%, 2%-10% and 2%-10% respectively.

In preferred embodiments of the invention, the conductive agent may be one or more of conductive carbon black, graphite, super P or carbon nanotubes.

In preferred embodiments of the invention, the binder may be one or more of PVDF (polyvinylidene fluoride), polytetrafluoroethylene, or sodium polyacrylate.

(3) The grinding mixture is placed in a vacuum drying oven and heated to 65° C. for 5 h to dry the moisture that may exist in the mixture to ensure that the sample is dry and the positive mixture is obtained.

(4) Drop 10 g of NMP (N-methyl-pyrrolidone) solvent in a dry glass bottle, and then slowly add the positive mixture to the glass bottle, and stir with a magnetic stirrer for 3 h, to ensure that the mixture is uniform, to get a solid content of 50% anode paste. The purpose of this step is to ensure that the components of the anode paste dispersed evenly, and the solid content and the viscosity of the anode paste has a certain relationship, 50% solid content of the anode paste viscosity is better, coated on the base after the film effect is better, can reduce the phenomenon of powder or rupture.

(5) The use of plate coating machine will be positive paste coated on the surface of the base, the conductive layer, and then the conductive layer and the base in a vacuum drying oven baking, heating to 110° C., for 12 h, to ensure that the water is completely dried.

In the preferred embodiment of the invention, the base material is one of aluminum foil or foam nickel mesh, and the thickness is 12-18 um.

In a preferred embodiment of the invention, the base material is aluminum foil with a thickness of 15 um.

(6) The use of electric vertical roller press on the conductive layer and the base of the roll, can make the overall thickness of the conductive layer and the base down to 180-220 um, get the anode plate finished product. By adjusting the working parameters of the coating machine and the roller press, the thickness of the anode plate can be controlled to ensure that the electrode plate can have a relatively perfect conductive network on the premise of higher compaction density, so as to meet the working requirements of large current pulse discharge.

Figure 5:
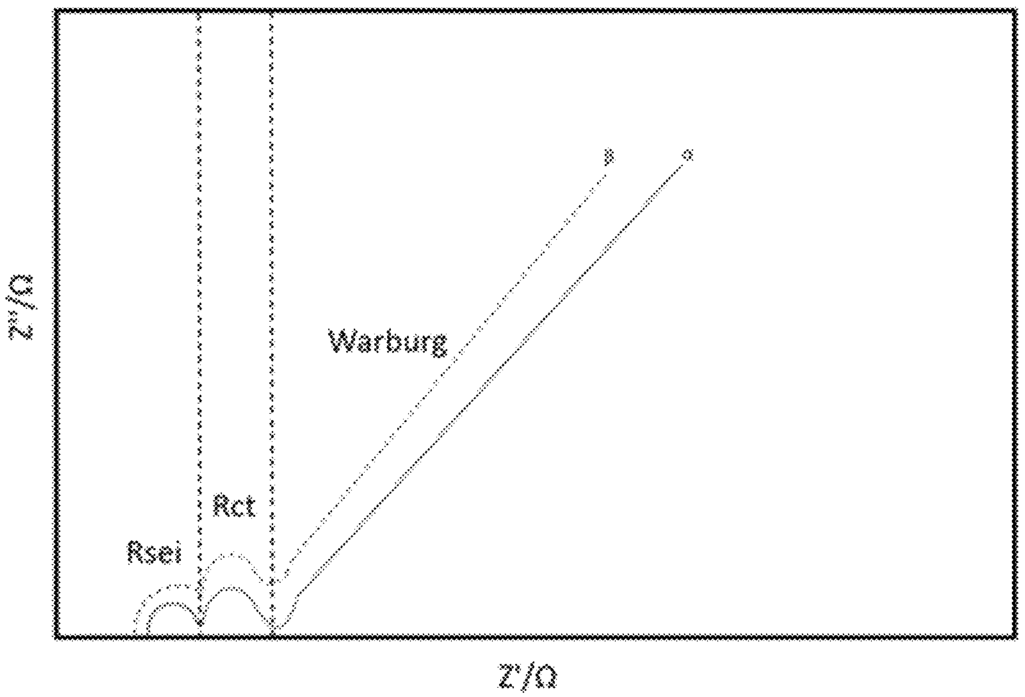
FIG. 5 is the contrast diagram of electrochemical impedance spectrum of the anode plate according to the first embodiment of the invention.

FIG. 5 is the contrast diagram of electrochemical impedance spectrum. The solid line a is the electrochemical impedance curve of the anode plate a processed according to the process steps of the embodiment of the present invention (coating method combining dry and wet mixture), and the dotted line B is the electrochemical impedance curve of the anode plate ß processed by the prior art process steps (tablet paste method). Can be seen from the diagram, in the stage of Rsei, the curvature of the solid line a is smaller than that of the dotted line B, indicating that the polarization degree of the anode plate a is smaller than that of the anode plate B, and the wetness of the electrolyte of the anode plate a is better than that of the anode plate ß, so when large current pulse discharge, the resistance of a is smaller than that of B, which improves the discharge capacity of the battery. Secondly, in the stage of Rct, the curvature of the solid line a is still smaller than the curvature of the dotted line B, indicating that the resistance of the anode plate a is smaller than that of the anode plate B. This is because the porosity of the anode plate a is larger than that of the anode plate ß in the same environment in the battery. The anode plate a can accommodate more and higher concentration of electrolyte. The discharge capacity of the battery under large current pulse is further improved.

In an embodiment of the invention, the cathode plate 1235 is mainly lithium base material.

In embodiments of the invention, the material of the diaphragm 1232 is PE (polyethylene) or PP (polypropylene), which can be a single layer of PE or PP or three layers of PE or PP.

In the embodiment of the present invention, the end A of the pole ear 1236 is fixedly connected with the anode plate 1234 or the cathode plate 1235. In the preferred embodiment of the present invention, the end A is fixedly connected with the anode plate 1234 or the cathode plate 1235 through tin welding or solder paste.

In an embodiment of the invention, the pole ear 1236 connected to the anode plate is made of aluminum, and the pole ear 1236 connected to the cathode plate is made of nickel or copper-plated nickel.

In the embodiment of the invention, a through-hole is also arranged on the side wall of the cavity shell 1231, and the other end B of the polar ear 1236 passes through the through-hole from the inside of the cavity shell to the outside of the cavity shell, and the connection between the outer end B of the cavity shell and the through-hole is coated with insulation adhesive to realize the fixed connection between the polar ear 1236 and the cavity shell 1231. Meanwhile, the end B of the pole ear 1236 is fixedly connected with the end C of wire 126.

In the embodiment of the invention, the other end D of wire 126 is electrically connected to the internal circuit 125.

In the preferred embodiment of the invention, the end B of pole ear 1236 is fixedly connected with wire 126 by solder. In the preferred embodiment of the invention, sealing materials, such as hot melt adhesive or silica gel, are coated at the connection point between the end B of pole ear 1236 and the end C of wire 126 and the connection point between the end B of pole ear 1236 and the through-hole, on the one hand, to prevent electrolyte leakage outside the battery cavity 123 and cause pollution; On the other hand, prevent the end B of the pole ear 1236 from being exposed on the cavity housing 1231, and avoid unnecessary battery discharge.

Specifically, in the embodiment of the invention, the processing process of battery cavity 123 is as follows:

(1) Coat the inside of the upper cover shell 12311 and the lower shell 12312 with PET or TPE material with a thickness of 300-500 um. Put it in a constant temperature oven and set the temperature 60-85° C. until the coating material is completely dry;

(2) the battery (comprising cathode plate 1235, cathode pole ear 1236, diaphragm 1232, anode plate 1234, anode pole ear 1236) placed in the lower shell 12312, one end of the positive and cathode pole ear 1236 is fixed on the through-hole of the side wall of the cavity shell 1231 through the solder, at the same time, the other end of the positive and cathode pole ear 1236 is respectively connected with the positive and cathode plate by solder or solder paste;

(3) The lower shell 12312 was placed in a static position, and electrolyte 1233 is injected into the lower shell 12312 with a pipette gun, and the whole is moved to the vacuum chamber for static position to ensure the complete infiltration of the electrolyte, so as to improve the electrochemical performance of the battery cavity;

(4) After the end of the lower shell 12312 standing, the upper cover shell 12311 shall be closed, and sealant shall be coated at the joint of the cover and closure to maintain the sealing property and obtain a complete battery cavity.

Continue to refer to FIG. 1, the electrical contact 122 and connector 114 form an electrical connection, on the sensor bottom case 111, connector 114 is arranged around groove 131, used to place the sealing ring 130, sealing ring contour is consistent with the groove contour, groove 131 and sealing ring 130 constitute waterproof structure, provide waterproof protection for the electrical connection between transmitter 12 and sensor 11.

In other embodiments of the invention, the contour of the sealing ring may also be inconsistent with the contour of the groove, for example, the groove is square, round, arc or a combination thereof, and the corresponding sealing ring is round, arc, square or a combination thereof.

Figure 6A:
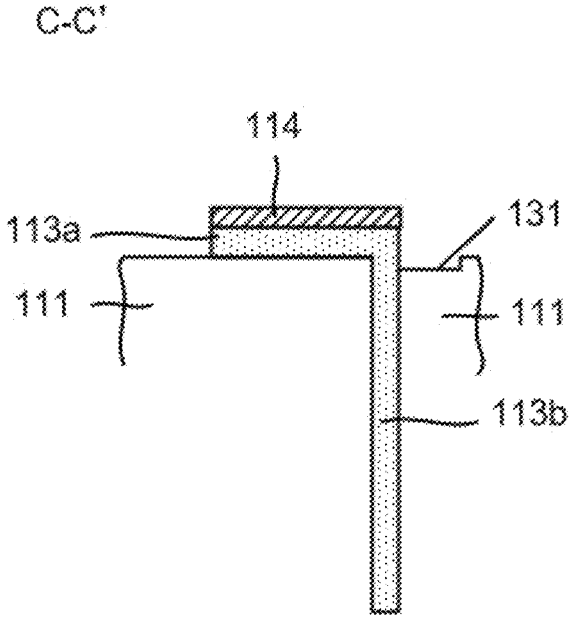
FIG. 6*a* is the C-C' section of the sensor shown in FIG. 2 before mounting the sealing ring according to the first embodiment of the present invention.
Figure 6B:
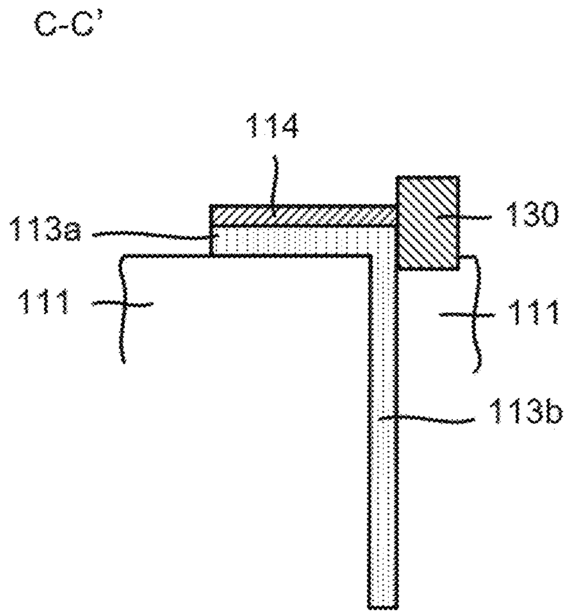
FIG. 6*b* is the C-C' section of the sensor shown in FIG. 2 after the sealing ring is installed according to the first embodiment of the present invention.
Figure 6C:
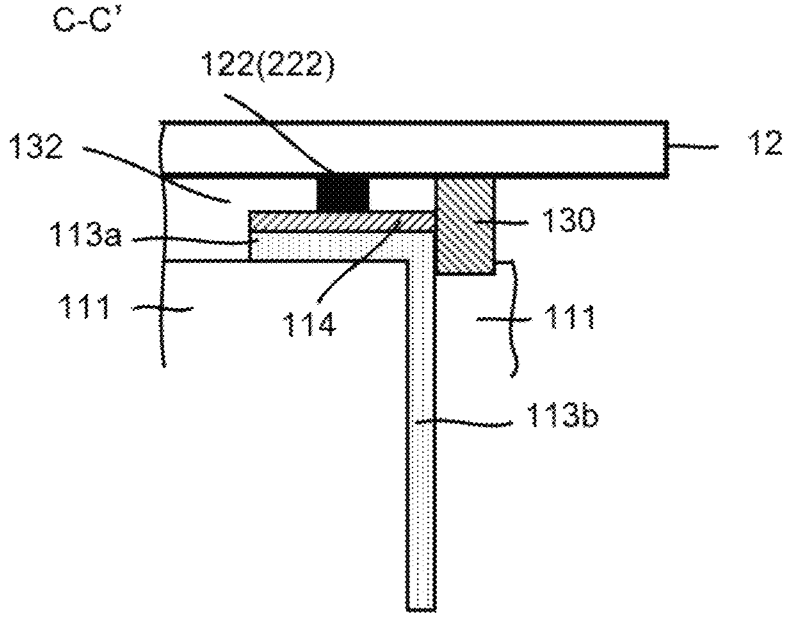
FIG. 6*c* is the C-C' section of the sensor shown in FIG. 2 after the sealing ring and transmitter are installed according to the first embodiment of the present invention.

For a clearer understanding of the waterproof principle of groove 131 and seal ring 130, refer to FIG. 6*a*, FIG. 6*b* and FIG. 6*c*.

FIG. 6*a* shows the C-C' section of sensor 11 as shown in FIG. 2 before the installation of sealing ring 130. Groove 131 is arranged on the sensor bottom case 111 around probe 113 and conductive silica gel 114. Probe 113 is divided into internal part 113*b* and external part 113*a*. The external part 113*a* is bent or bent towards the upper end of the sensor bottom case 111, and is tiled on the sensor bottom case 111. FIG. 6*b* shows the C-C' section of sensor 11 as shown in FIG. 2 after the installation of sealing ring 130. The section of sealing ring 130 is consistent with that of groove 131. The sealing ring 130 fits closely to groove 131, probe 13 and connector 114, and the upper face of sealing ring 130 is slightly higher than that of connector 114. Here, "slightly higher" means that the upper end face of sealing ring 130 is 0~5 mm higher than the upper end face of connector 114, preferably 1 mm. FIG. 6*c* shows the C-C' section of sensor 11 as shown in FIG. 2 after installing the sealing ring 130 and transmitter module 12. The electrical contact 122 is in contact with connector 114, and the transmitter housing is in contact with the upper surface of the sealing ring 130. It can be foreseen that the transmitter housing 12, sealing ring 130 and groove 131 can form a sealed chamber 132. The external part of the probe 113*a*, connector 114 and electrical contact 122 are located in the chamber 132. When the detection device enters underwater, water droplets are blocked by transmitter housing 12, sealing ring 130 and groove 131, and cannot enter the containment chamber 132, thus forming waterproof protection for the electrical connection area of electrical contact 122 and connector 114.

In other embodiments of the invention, the size of the sealing ring is slightly larger than the size of the groove, which enables the sealing ring 130 to be more tightly fitted into the groove 131 and not easy to fall off, and the edge of the sealing ring 130 to form a more closed contact with the groove 131 and achieve more ideal waterproof protection.

In other embodiment of the invention, a sealing ring (not shown in the figure) can also be added below the outer part of the probe 113*a* and above the sensor bottom case 111 to form a waterproof structure together with the sealing ring and groove above the outer part of the probe 113*a*, which can better prevent water droplets from entering the electric connection area and achieve a better waterproof effect.

In other embodiment of the invention, the sealing ring material is preferred as insulating rubber, as rubber is flexible material, and has a certain compressive elasticity, when the transmitter 12 is installed on the bottom case 10, there is a certain extrusion pressure on the sealing ring 130, which can better maintain the close contact between the sealing ring 130 and the shell of the transmitter 12, to prevent water droplets into the electric connection area, avoid causing short circuit and current intensity disturbance.

Second Embodiment

Figure 7:
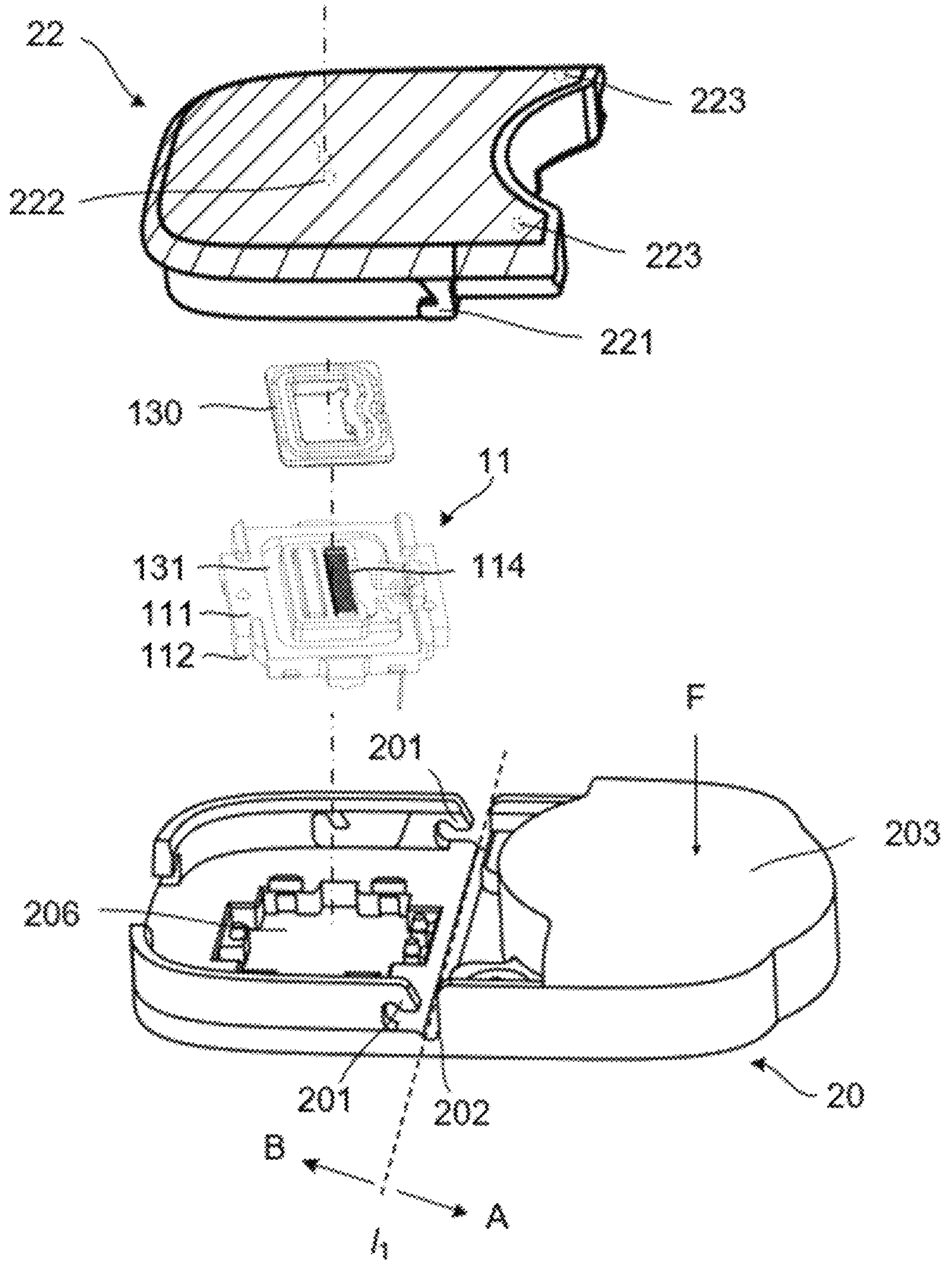
FIG. 7 is the schematic diagram of the highly integrated analyte detection device according to the second embodiment of the invention.

FIG. 7 is a schematic diagram of a highly integrated analyte detection device according to the second embodiment of the invention.

The detection device comprises the bottom case 20, the sensor 11, the transmitter 22 and the battery cavity 203.

Combined with the schematic diagram of the three-dimensional structure of the sensor shown in FIG. 2, sensor 11 is installed on the bottom case 20, comprising at least probe 113 and connector 114. The probe 113 is used to pierce into human skin to detect the parameters of body fluid analyte and convert them into electrical signals, which are transmitted to the electrical contact 122 of transmitter 12 through connector 114. Transmitter 12 then transmits fluid analyte parameter information to the user.

In an embodiment of the invention, the connector 114 comprises at least two conductive and insulating zones. Conductive zone and insulating zone play the role of electrical conduction and electrical insulation respectively. The conductive zone and the insulating zone can't be separated from each other, that is, the conductive zone and the insulating zone respectively belong to the whole part of the connector 114. Connector 114 can conduct electricity only longitudinally through the conductive zone, which insulates the conductive zones from each other and therefore cannot conduct electricity horizontally. A connector 114 plays the role of electrical conductivity and electrical insulation at the same time, the complexity of the internal structure of the detection device is reduced, the internal structure is more compact, and the integration of the detection device is improved.

In other embodiments of the invention, the connection $l_1$ of the two second clamping parts 202 divides the bottom case 20 into side A and side B. Side A is provided with a force application part, Side B is provided with a fixing part.

In an embodiment of the invention, the fixing part and the force application part are relative concepts. According to the structural design of the bottom case 20 and the transmitter 22, the position of the fixing part and the force application part can be selected differently.

Case, the implementation of the present invention, therefore, the separation of bottom case 20 and transmitter 22 process is as follows: fixed with finger side B fixed units, with another finger along a direction of applying force F, get the second card in 202, which separated the second card 202 and the first card 221, separate the transmitter 22 and bottom case 20.

It should be noted that the embodiment of the invention does not limit the position of the second clamping part 202. For example, the two second clamping parts 202 can be set on the bottom plate of the bottom case 20, and there is no specific restriction here.

The embodiment of the invention has no specific restriction on the shape of the top view of the detection device, and the shape can also be rounded rectangle, rectangle, circle, oval or other shapes.

The battery cavity 203 is used to supply power to the transmitter and is arranged on the bottom case 20. In this way, the battery cavity 203 can be replaced every time the bottom case 20 is replaced. Transmitter 22 can be reused all the time because no battery is set, which reduces the cost of replacing transmitter 22. Meanwhile, the bottom case 20 always uses a new high-performance battery cavity, which can ensure the continuous high performance working state of transmitter 22.

Preferably, in embodiments of the invention, the top of the battery cavity 203 is flush with the top of the transmitter 22 so as to reduce the thickness size of the detection device.

Battery cavity 203 can be directly used as the force application part, so the battery is located on the Side A of $l_1$. As the battery cavity 203 has a relatively large area, it is easier for users to apply force to the battery cavity 203 as the force application part to optimize the user's operation steps.

Figure 8:
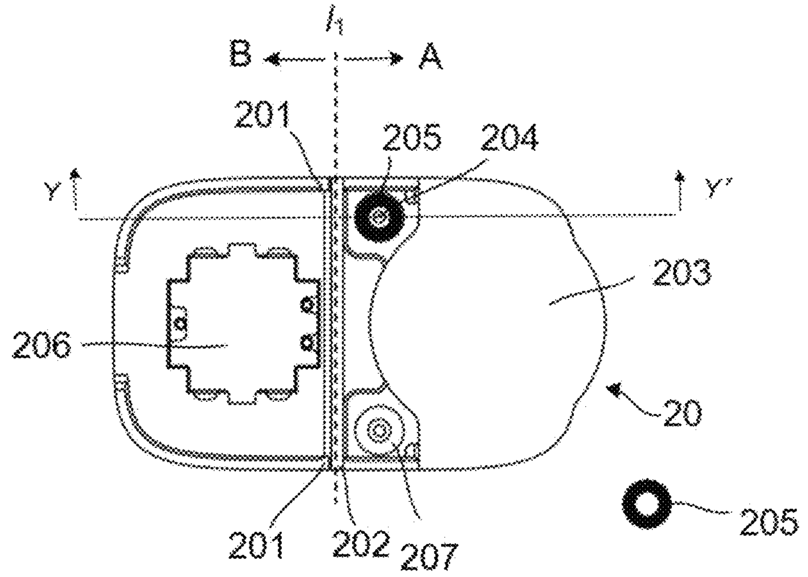
FIG. 8 is the top view of the bottom case according to the second embodiment of the invention.

FIG. 8 is a top view of bottom case 20 in an embodiment according to the invention.

Since the battery cavity 203 needs to supply power to transmitter 22, the bottom case 20 is also provided with at least two elastic conductors 204 in an embodiment of the invention. The electric contact 223 of transmitter 22 is electrically connected with the positive and cathodes of the battery respectively through the elastic conductive 204 to form the electric connection area. The battery cavity 203 supplies power to the transmitter 22 through an elastic conductor 204 and electrical contact 223, once the electric connection area enters into water droplets, short circuit will result in unstable power supply of battery cavity 203, and the current intensity received by transmitter 22 will fluctuate, which may cause the parameter information of body fluid analyte received by transmitter 22 from probe 113 and the parameter information transmitted by transmitter 22 to jump, affecting the reliability of analyte detection device, so it is necessary to waterproof the electrical connection area. The waterproof structure of the electrical connection area comprises a groove 207 and a sealing ring 205.

Figure 9A:
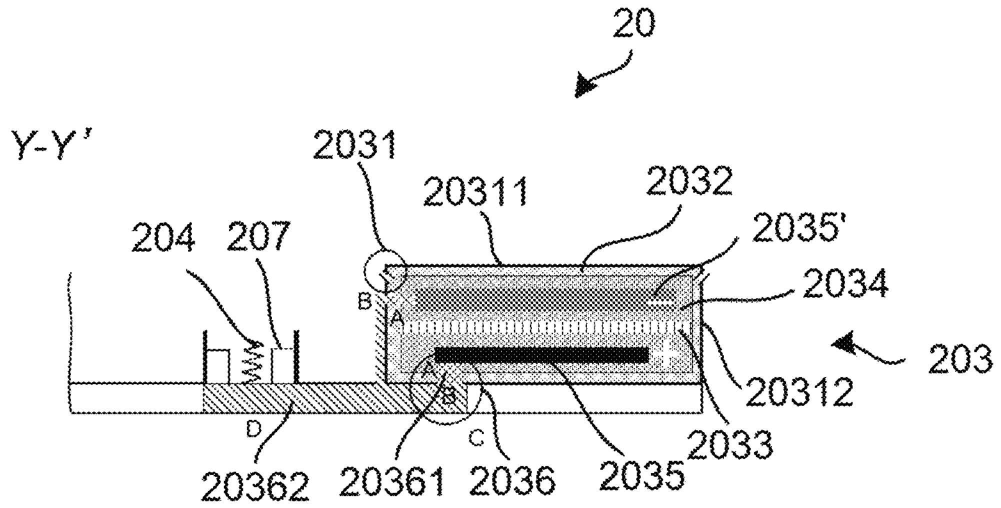
FIG. 9*a* is the Y-Y' section of the bottom case as shown in FIG. 8 before the sealing ring is installed according to the second embodiment of the invention.
Figure 9B:
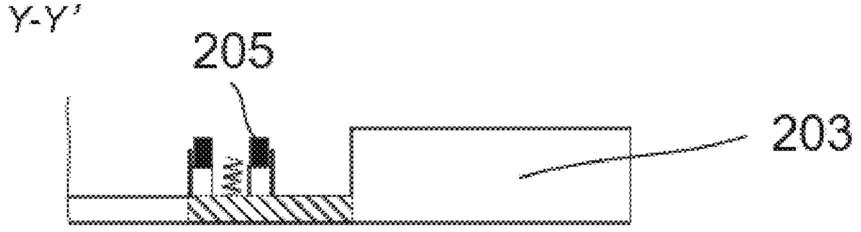
FIG. 9*b* is the Y-Y' section of the bottom case as shown in FIG. 8 after the sealing ring is installed according to the second embodiment of the invention.
Figure 9C:
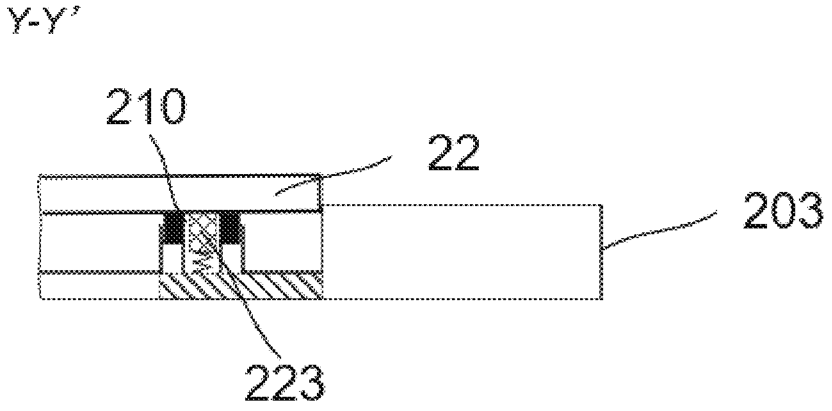
FIG. 9*c* is the Y-Y' section of the bottom case as shown in FIG. 8 after the sealing ring and transmitter are installed according to the second embodiment of the invention.

For a clearer understanding of the waterproof principle of the waterproof structure composed of groove 207 and sealing ring 205, as well as the structure of the battery cavity, refer to FIG. 9*a*, FIG. 9*b*, and FIG. 9*c*.

FIG. 9*a* shows the Y-Y' section of bottom case 20 before installation of sealing ring 205, as shown in FIG. 8. Battery cavity 203 comprises cavity shell 2031, electrolyte insulation layer 2032, diaphragm 2033, electrolyte 2034, anode plate 2035, cathode plate 2035' and pole ear 2036. The actual size and proportion of each part are not necessarily equal to the size and proportion of each part in FIG. 8.

In the embodiment of the invention, the material of cavity shell 2031 is one of PE, PP, HDPE, PVC, ABS, PMMA, PC, PPS or PU. Compared with the button battery with metal shell, the weight of the battery cavity 203 with plastic shell 2031 can be greatly reduced, thus reducing the overall weight of the analyte detection device. Improved user experience.

In an embodiment of the invention, the cavity shell 2031 is divided into the upper cover shell 20311 and the lower shell 20312. The upper cover shell 20311 is closed on the lower shell 20312, forming a closed chamber space inside, and the joint between the upper cover shell 20311 and the lower shell 20312 is coated with sealant.

In the preferred embodiment of the invention, the material of cavity shell 2031 is consistent with that of bottom case 20, which is convenient for integrated injection molding during processing and improves production efficiency. That is, the shell 2031 of the battery cavity 203 is part of the bottom case 20.

In an embodiment of the present invention, the section shape of cavity shell 2031 is not limited to the rectangle shown in the FIG., but can also be round, oval, triangular or other irregular shapes, and its three-dimensional structure can make full use of the available space between transmitter 12 and bottom casing 10 to adapt to the miniaturization design of analyte detection device.

In the embodiment of the invention, the cavity shell 2031 made of plastic material, such as PE (polyethylene), PP (polypropylene) and PC (polycarbonate), is easy to be corroded by the electrolyte, so it is necessary to coat the interior of the cavity shell 2031 with an electrolyte insulation layer 2032. In an embodiment of the invention, the electrolyte insulation layer 2032 can be TPE or PET (polyethylene terephthalate), TPE is a thermoplastic elastomer material with strong processing ability, PET itself as the container of the electrolyte, can effectively isolate the corrosion of the electrolyte to the cavity shell and circuit devices.

In embodiments of the invention, the electrolyte insulation layer 2032 may be either a thin film coated inside the cavity shell 2031 by deposition or solution method, or a separate shell layer.

In the preferred embodiment of the invention, the electrolyte insulation layer 2032 is a film of 300-500 um thickness. If the electrolyte isolation layer 2032 is too thin, the membrane will be infiltrated and softened by the electrolyte, which will lead to aging of the membrane after a long time. If the electrolyte isolation layer 2032 is too thick, will occupy the space of the battery cavity. In a preferred embodiment of the invention, the thickness of the electrolyte insulation layer 2032 is 400 um.

In an embodiment of the invention, the solute of electrolyte 2034 is lithium salt, such as one of lithium perchlorate ($LiClO_4$), lithium hexafluorophosphate ($LiPF_6$), lithium tetrafluoroborate ($LiBF_4$). The solvent is one of vinyl carbonate, propylene carbonate, diethyl carbonate, dimethyl carbonate, methyl carbonate, phosphorus pentafluoride, hydrofluoric acid, ether, ethylene carbonate, propylene carbonate, diethyl carbonate. In the preferred embodiment of the invention, the solvent is organic solvent, such as ether, ethylene carbonate, propylene carbonate, diethyl carbonate.

In an embodiment of the invention, the main material of the anode plate 2035 is manganese dioxide and is prepared by the following process:

(1) The electrolytic manganese dioxide, conductive agent and binder were screened through a screen or air classifier, select the particle size less than 200 um electrolytic manganese dioxide particles, placed in the quartz boat, heat treatment was carried out in the sintering furnace and the temperature was heated to 200° C. for 4 h. The purpose of this step is to make electrolytic manganese dioxide lose part of binding water, X-ray diffraction peak shift, crystal plane spacing decrease, Mn—O bond force increase, so as to enhance the discharge capacity of electrolytic manganese dioxide.

(2) After the electrolytic manganese dioxide in step (1) is cooled to below 60° C., an electronic balance is used to weigh 9 g electrolytic manganese dioxide, 0.5 g conductive agent with particle size less than 200 um, and 0.5 g binder with particle size less than 200 um, put them in the grinding dish, fully stir and mix, then grind manually or electrically to get 10 g grinding mixture. And allows the grinding mixture to pass through a screen of 300 mesh (size 48 um). The purpose of this step is to ensure the uniformity of the mixture and avoid the phenomenon of uneven dispersion of conductive agent and binder.

In other embodiments of the invention, the mass proportion of electrolytic manganese dioxide, conductive agent and binder is not limited to the above proportion, and the mass proportion can be 80%-96%, 2%-10% and 2%-10% respectively.

In preferred embodiments of the invention, the conductive agent may be one or more of conductive carbon black, graphite, super P or carbon nanotubes.

In preferred embodiments of the invention, the binder may be one or more of PVDF (polyvinylidene fluoride), polytetrafluoroethylene, or sodium polyacrylate.

(3) The grinding mixture is placed in a vacuum drying oven and heated to 65° C. for 5 h to dry the moisture that may exist in the mixture to ensure that the sample is dry and the positive mixture is obtained.

(4) Drop 10 g of NMP (N-methyl-pyrrolidone) solvent in a dry glass bottle, and then slowly add the positive mixture to the glass bottle, and stir with a magnetic stirrer for 3 h, to ensure that the mixture is uniform, to get a solid content of 50% anode paste. The purpose of this step is to ensure that the components of the anode paste dispersed evenly, and the solid content and the viscosity of the anode paste has a certain relationship, 50% solid content of the anode paste viscosity is better, coated on the base after the film effect is better, can reduce the phenomenon of powder or rupture.

(5) The use of plate coating machine will be positive paste coated on the surface of the base, the conductive layer, and then the conductive layer and the base in a vacuum drying oven baking, heating to 110° C., for 12 h, to ensure that the water is completely dried.

In the preferred embodiment of the invention, the base material is one of aluminum foil or foam nickel mesh, and the thickness is 12-18 um.

In a preferred embodiment of the invention, the base material is aluminum foil with a thickness of 15 um.

(6) The use of electric vertical roller press on the conductive layer and the base of the roll, can make the overall thickness of the conductive layer and the base down to 180-220 um, get the anode plate finished product. By adjusting the working parameters of the coating machine and the roller press, the thickness of the anode plate can be controlled to ensure that the electrode plate can have a relatively perfect conductive network on the premise of higher compaction density, so as to meet the working requirements of large current pulse discharge.

The performance of the anode plate 2035 obtained through the above steps is consistent with that shown in FIG. 5 and will not be repeated here.

In an embodiment of the invention, the cathode plate 2035' is mainly lithium base material.

In an embodiment of the invention, the material of the diaphragm 2033 is PE (polyethylene) or PP (polypropylene), which can be a single layer of PE or PP, or three layers of PE or PP.

In an embodiment of the invention, the anode material of the battery pole ear 2036 is aluminum, and the cathode material is nickel or copper-plated nickel.

In the embodiment of the invention, the pole ear 2036 comprises A conductive contact 20361 and A conductive strip 20362, and the end part A of the conductive contact 20361 is fixedly connected with the anode plate 2035 or the cathode plate 2035'. In the preferred embodiment of the invention, end A is fixedly connected with the positive or cathode plate 2035 by tin welding or solder paste.

In the embodiment of the invention, a through-hole is also arranged on the side wall of the cavity shell 2031, the other end B of the conductive contact 20361 passes through the through-hole from the inside of the cavity shell to the outside of the cavity shell, and the connection between the outer end B of the cavity shell and the through-hole is coated with sealant, so as to realize the fixed connection between the pole ear 2036 and the cavity shell 2031. In the preferred embodiment of the invention, end B of the conductive contact 20361 is fixedly connected with the cavity shell 2031 by soldering.

In an embodiment of the invention, one end C of the conductive strip 20362 is fixedly connected with end B of the conductive contact 20361.

In the embodiment of the invention, the fixed connection between the end C of the conductive strip 20362 and the end B of the conductive contact 20361, and the connection between the end B of the electrical contact 20361 and the through-hole are also coated with insulating sealing materials, such as hot melt adhesive or silica gel, on the one hand, to prevent the electrolyte 2034 from leaking to the outside of the cavity shell 2031 through the through-hole, causing pollution; On the other hand, the end B of the pole ear 2036 is not exposed on the cavity shell 2031, so as to avoid unnecessary battery discharge.

Specifically, in the embodiment of the invention, the processing process of battery cavity 203 is as follows:

(1) Coat PET or TPE material inside the upper cover shell 20311 and the lower shell 20312 with a thickness of 300-500 um, and then put them in a constant temperature oven and set the temperature 60-85° C. until the coating material is completely dry;

(2) the battery (comprising the cathode plate 2035', the cathode pole ear 2036, diaphragm 2033, anode plate 2035, anode pole ear 2036 are successively fixed in the lower shell 20312, and one end of the positive and cathode pole ear 2036 is fixed on the through-hole of the side wall of the cavity shell 2031 through tin paste, at the same time the other end of the positive and cathode pole ear 2036 respectively through solder or solder paste and positive and cathode plate fixed connection;

(3) The lower shell 20312 is placed in a static position, and electrolyte 2034 is injected into the lower shell 20312 with a pipette gun, and the whole is moved to the excessive chamber for vacuum standing to ensure the complete infiltration of the electrolyte, so as to improve the electrochemical performance of the battery cavity;

(4) After the end of the lower shell 20312 standing, the upper cover shell 20311 is closed, and sealant is coated at the joint of the cover closure to maintain the tightness and obtain a complete battery cavity.

In the embodiment of the present invention, the other end D of the conductive strip 20362 extends out of the battery cavity 203 to groove 207 and covers the bottom end face of groove 207, the elastic conductive 204 is located in the middle of groove 207, and one end is fixed on the end D of the conductive strip 20362. The conductive strip 20362 connected to the positive plate 2035 is the anode, and the conductive strip 20362 connected to the cathode plate 2035' is the cathode.

In the preferred embodiment of the invention, the elastic conductive 204 is a conductive spring.

FIG. 9*b* shows the Y-Y' section of bottom case 20 as shown in FIG. 8 after the installation of sealing ring 205. The sealing ring 205 is located on the upper end face of groove 207, and its contour is consistent with that of the groove, and it can envelope the elastic conductive 204. The upper end face of sealing ring 205 is slightly higher than that of groove 207. Here, "slightly higher" means that the upper end face of sealing ring 205 is 0~5 mm higher than the upper end face of groove 207, preferably 1 mm. FIG. 9*c* shows the Y-Y' section of the bottom case 20 as shown in FIG. 8 after installing the sealing ring 205 and transmitter 22. The transmitter power electrode 223 contacts the elastic conductive 204 to obtain the electric energy of battery cavity 203, and the transmitter 22 housing contacts the upper surface of the sealing ring 205. It can be foreseen that the transmitter 22 housing, sealing ring 205, groove 207 and conductive strip 20362 form a sealed chamber 210, and the transmitter power electrode 223 and elastic conductive 204 are located in the sealed chamber 210. When the detection device enters underwater, the water droplets are blocked by the transmitter 22 shell, the sealing ring 205 and the groove 207, and cannot enter the chamber 210, thus forming waterproof protection for the electric connection area of the transmitter power electrode 223, the elastic conductive 204 and the conductive strip 20362.

In other embodiments of the invention, the size of the sealing ring is slightly larger than the size of the groove, which enables the sealing ring 205 to be fitted more tightly into the groove 207 and is not easy to fall off, and the edge of the sealing ring 205 can form a more closed contact with the groove 207 and achieve more ideal waterproof protection.

In other embodiments of the present invention, the material of elastic conductive 204 is an elastic conductive material that can be electrically connected with the transmitter power electrode 223, such as can be conductive spring or conductive shrapnel. When transmitter 22 is installed on the bottom case 20, the transmitter power electrode 223 squeezes the elastic conductive 204 so that the elastic conductive 204 continues to compress and maintain its elasticity. In this way, the elastic conductor 204 can maintain continuous close contact with the transmitter power electrode 223 to ensure that the battery cavity 203 transmits stable power to transmitter 22

In other embodiments of the present invention, the sealing ring material is preferably insulation rubber. As the rubber is a flexible material and has a certain compressive elasticity, when the transmitter 22 is installed on the bottom case 20, there is a certain extrusion pressure on the sealing ring 205, which can better maintain the close contact between the sealing ring 205 and the shell of transmitter 22, to prevent water droplets into the electric connection area, avoid causing short circuit and current intensity disturbance.

Third Embodiment

Figure 10:
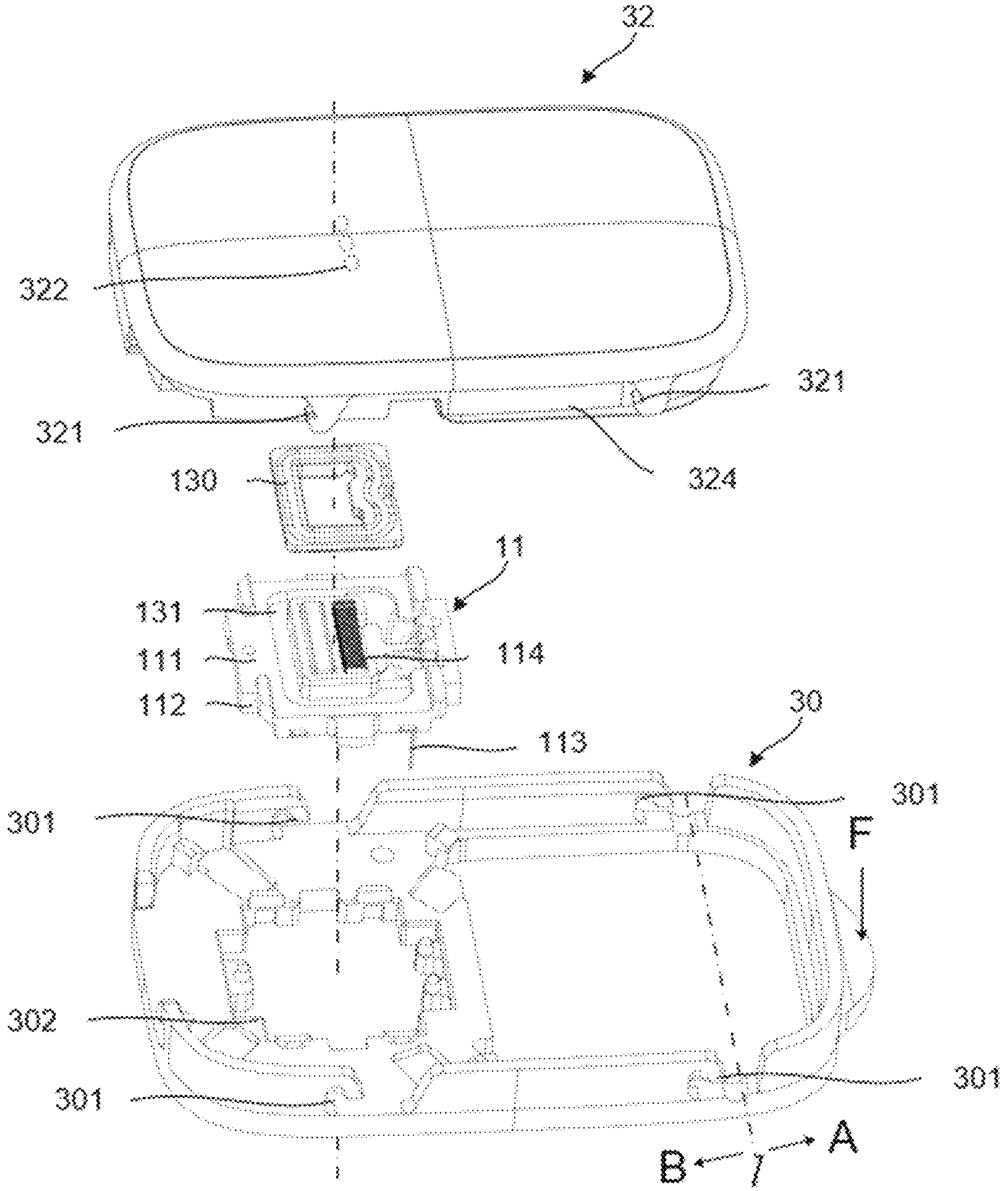
FIG. 10 is the schematic diagram of the highly integrated analyte detection device according to the third embodiment of the invention.

FIG. 10 is a schematic diagram of a highly integrated analyte detection device according to the third embodiment of the invention.

The detection device comprises the bottom case 30, the sensor 11, the transmitter module 32 and the battery cavity 323.

The bottom case 30 is used to assemble transmitter module 32 and sensor 11, and the detection device is glued to the skin surface by the bottom adhesive tape (not shown). The bottom case 30 comprises a fixing part and a force application part. The bottom case 30 is provided with at least one second clamping part 301. The second clamping part 301 is used to clamping the transmitter module 32. Specifically, in an embodiment of the invention, the number of the second clamping part 301 is two. The two second clamping parts 301 correspond to the side walls of the bottom case 30.

Here, the fixing part and the force application part are relative concepts. According to the structural design of the bottom case 30 and the transmitter module 32, the position of the fixing part and the force application part can be selected differently, which will be described in detail below.

Transmitter module 32 is provided with at least one first clamping part 321. The first clamping part 321 corresponds to the second clamping part 301. The transmitter module 32 is mounted on the bottom case 30 by clamping the second part 301 and the first part 321. Obviously, in an embodiment of the invention, the transmitter module 32 is provided with two first clamping parts 321, that is, two pairs of mutually clamping first clamping parts 321 and second clamping parts 301.

Here, the first clamping part 321 corresponds to the second clamping part 301, which means that they have the same quantity and corresponding position.

When separating bottom case 30 and transmitter module 32, the fixing part is fixed by finger or other equipment, using another finger or other auxiliary equipment in one direction to apply force on the force application part, bottom case 30 will fail, the second clamping part 301 and the first clamping part 321 are separated from each other, and then the transmitter module 32 and bottom case 30 are separated. That is, when the user separates the bottom case 30 and the transmitter module 32, only one finger applies force to the force application part in one direction to separate the two, which is convenient for the user to operate. After separation, the transmitter can be reused, reducing the cost to the user.

It should be noted here that failure is a common concept in the field of engineering materials. After failure, the material loses its original function and the failure part cannot be restored again. Since the second clamping part 301 is part of the bottom case 30, the failure of bottom case 30 comprises the failure of bottom plate, side wall or the second clamping part 301 of bottom case 30. Therefore, the failure modes of bottom case 30 include bottom or side wall fracture of bottom case 30, bottom case 30 damage, second clamping part 301 fracture, bottom case 30 plastic deformation of one or more. Obviously, after the failure of the bottom case 30, the bottom case 30 loses the function and function of clamping transmitter module 32.

The way of fixing the fixing part comprises clamping, supporting and other ways. There are no specific restrictions here, as long as the conditions for fixing the fixing part can be met.

Combined with the schematic diagram of the three-dimensional structure of the sensor shown in FIG. 2, sensor 11 is installed on the bottom case 30, comprising at least probe 113 and connector 114. The probe 113 is used to pierce into human skin to detect the parameters of body fluid analyte and convert them into electrical signals, which are transmitted to the electrical contact 322 of transmitter module 32 through connector 114. Transmitter module 32 then transmits analyte parameter information to the user.

In an embodiment of the invention, the connector 114 comprises at least two conductive and insulating zones. Conductive zone and insulating zone play the role of electrical conduction and electrical insulation respectively. The conductive zone and the insulating zone can't be separated from each other, that is, the conductive zone and the insulating zone respectively belong to the whole part of the connector 114. Connector 114 can conduct electricity only longitudinally through the conductive zone, which insulates the conductive zones from each other and therefore cannot conduct electricity horizontally. A connector 114 plays the role of electrical conductivity and electrical insulation at the same time, the complexity of the internal structure of the detection device is reduced, the internal structure is more compact, and the integration of the detection device is improved.

Figure 11:
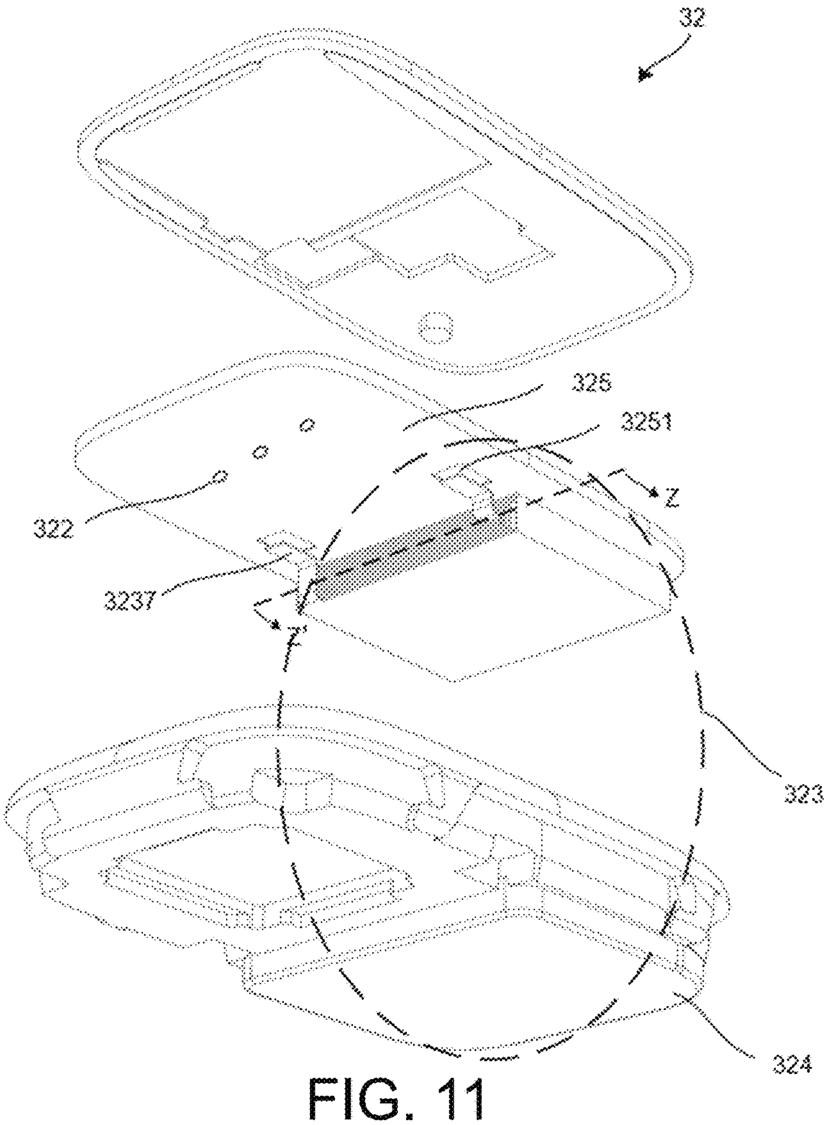
FIG. 11 is the internal structure of the transmitter module according to the third embodiment of the invention.
Figure 12:
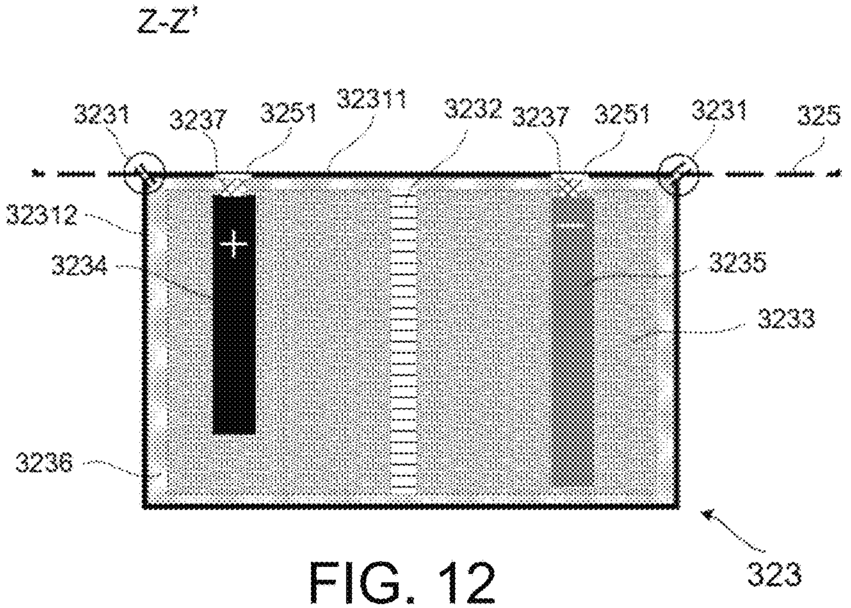
FIG. 12 is the schematic diagram of the Z-Z' section structure of the battery cavity according to the third embodiment of the invention.

FIG. 11 is the internal structure of the transmitter according to the third embodiment of the invention; FIG. 12 is a schematic diagram of the Z-Z' section structure of the battery cavity.

In combination with FIGS. 11 and 12, in the embodiment of the invention, battery cavity 323 is located in transmitter module 32, the upper cover shell 32311 of battery cavity shell 3231 is circuit board 325, and the lower shell 32312 is transmitter shell 324, so as to form a good seal and prevent electrolyte leakage. And prevent external air, water droplets and other debris into the battery cavity 323.

In an embodiment of the invention, the battery cavity 323 comprises the cavity shell 3231, the diaphragm 3232, the electrolyte 3233, the anode plate 3234, the cathode plate 3235 and the conductive strip 3237. The actual size and proportion of each part are not necessarily equal to the size and proportion of each part in FIG. 12.

In an embodiment of the invention, the battery cavity 323 is electrically connected with the power electrode 3251 of the circuit board 325 through a conductive strip 3237 to supply power to the internal circuit 325.

In the embodiment of the invention, the cavity shell 3231 is made of one of PE, PP, HDPE, PVC, ABS, PMMA, PC, PPS or PU. Compared with the button battery with metal shell, the weight of the battery cavity 3231 made of plastic shell 3231 can be greatly reduced, thus reducing the overall weight of the analyte detection device, which improves users' experience.

In an embodiment of the invention, the cavity shell 3231 is divided into an upper cover shell 32311 and a lower shell 32312. The upper cover shell 32311 is a part of the circuit board 325, and the anode plate 3234 and the cathode plate 3235 are electrically connected with the power electrode 3251 of the circuit board 325 through the conductive strip 3237, so as to realize the closed loop of the battery cavity 323, and the battery cavity 323 can provide electric energy for the circuit board 325.

In an embodiment of the invention, the lower shell 32312 is a cavity shell which is independent of the shell of transmitter module 324.

In other embodiments of the invention, the material of the lower shell 32312 is consistent with that of the transmitter module shell 324, which is convenient for integrated injection molding during processing and improves production efficiency.

In an embodiment of the invention, the upper cover shell 32311 is closed on the lower shell 32312, and a closed chamber space is formed inside. Sealant is coated at the connection between the upper cover shell 32311 and the lower shell 32312.

In embodiments of the invention, the sealant is one of hot melt adhesive or silica gel.

In an embodiment of the invention, a cavity shell 3231 made of plastic, such as PE (polyethylene), PP (polypropylene) and PC (polycarbonate), is easy to be corroded by the electrolyte, so it is necessary to set an electrolyte insulation layer 3236 inside the cavity shell 3231.

In an embodiment of the present invention, the section shape of cavity shell 3231 is not limited to the rectangle shown in the figure, but can also be round, oval, triangular or other irregular shapes, and its three-dimensional structure can make full use of the available space between transmitter module 32 and bottom case 30 to adapt to the miniaturization design of analyte detection device.

In an embodiment of the invention, the electrolyte insulation layer 3237 can be TPE or PET (polyethylene terephthalate). TPE is a thermoplastic elastomer material with strong processing ability. PET itself acts as the container of the electrolyte and can effectively isolate the corrosion of the electrolyte to the cavity shell and circuit devices.

In embodiments of the present invention, the electrolyte insulation layer 3237 may be a film coated inside the cavity shell 3231 by deposition or solution method or a closed shell independent of the cavity shell.

In the preferred embodiment of the invention, the electrolyte insulation layer 3237 is a film of 300-500 um thickness. If the electrolyte isolation layer 3237 is too thin, the membrane will be infiltrated and softened by the electrolyte, which will lead to aging of the membrane after a long time. If the electrolyte isolation layer 3237 is too thick, will occupy the space of the battery cavity. In a preferred embodiment of the invention, the thickness of the electrolyte insulation layer 3237 is 400 um.

In an embodiment of the invention, the solute of electrolyte 3233 is lithium salt, such as one of lithium perchlorate ($LiClO_4$), lithium hexafluorophosphate ($LiPF_6$), lithium tetrafluoroborate ($LiBF_4$). The solvent is one of vinyl carbonate, propylene carbonate, diethyl carbonate, dimethyl carbonate, methyl carbonate, phosphorus pentafluoride, hydrofluoric acid, ether, ethylene carbonate, propylene carbonate, diethyl carbonate. In the preferred embodiment of the invention, the solvent is organic solvent, such as ether, ethylene carbonate, propylene carbonate, diethyl carbonate.

In an embodiment of the invention, the main material of the anode plate 3234 is manganese dioxide and is prepared by the following process:

(1) The electrolytic manganese dioxide, conductive agent and binder were screened through a screen or air classifier, select the particle size less than 200 um electrolytic manganese dioxide particles, placed in the quartz boat, heat treatment was carried out in the sintering furnace and the temperature was heated to 200° C. for 4 h. The purpose of this step is to make electrolytic manganese dioxide lose part of binding water, X-ray diffraction peak shift, crystal plane spacing decrease, Mn—O bond force increase, so as to enhance the discharge capacity of electrolytic manganese dioxide.

(2) After the electrolytic manganese dioxide in step (1) is cooled to below 60° C., an electronic balance is used to weigh 9 g electrolytic manganese dioxide, 0.5 g conductive agent with particle size less than 200 um, and 0.5 g binder with particle size less than 200 um, put them in the grinding dish, fully stir and mix, then grind manually or electrically to get 10 g grinding mixture. And allows the grinding mixture to pass through a screen of 300 mesh (size 48 um). The purpose of this step is to ensure the uniformity of the mixture and avoid the phenomenon of uneven dispersion of conductive agent and binder.

In other embodiments of the invention, the mass proportion of electrolytic manganese dioxide, conductive agent and binder is not limited to the above proportion, and the mass proportion can be 80%-96%, 2%-10% and 2%-10% respectively.

In preferred embodiments of the invention, the conductive agent may be one or more of conductive carbon black, graphite, super P or carbon nanotubes.

In preferred embodiments of the invention, the binder may be one or more of PVDF (polyvinylidene fluoride), polytetrafluoroethylene, or sodium polyacrylate.

(3) The grinding mixture is placed in a vacuum drying oven and heated to 65° C. for 5 h to dry the moisture that may exist in the mixture to ensure that the sample is dry and the positive mixture is obtained.

(4) Drop 10 g of NMP (N-methyl-pyrrolidone) solvent in a dry glass bottle, and then slowly add the positive mixture to the glass bottle, and stir with a magnetic stirrer for 3 h, to ensure that the mixture is uniform, to get a solid content of 50% anode paste. The purpose of this step is to ensure that the components of the anode paste dispersed evenly, and the solid content and the viscosity of the anode paste has a certain relationship, 50% solid content of the anode paste viscosity is better, coated on the base after the film effect is better, can reduce the phenomenon of powder or rupture.

(5) The use of plate coating machine will be positive paste coated on the surface of the base, the conductive layer, and then the conductive layer and the base in a vacuum drying oven baking, heating to 110° C., for 12 h, to ensure that the water is completely dried.

In the preferred embodiment of the invention, the base material is one of aluminum foil or foam nickel mesh, and the thickness is 12-18 um.

In a preferred embodiment of the invention, the base material is aluminum foil with a thickness of 15 um.

(6) The use of electric vertical roller press on the conductive layer and the base of the roll, can make the overall thickness of the conductive layer and the base down to 180-220 um, get the anode plate finished product. By adjusting the working parameters of the coating machine and the roller press, the thickness of the anode plate can be controlled to ensure that the electrode plate can have a relatively perfect conductive network on the premise of higher compaction density, so as to meet the working requirements of large current pulse discharge.

The performance of the anode plate 3035 obtained through the above steps is consistent with that shown in FIG. 5 and will not be repeated here.

In an embodiment of the invention, the cathode plate 3235 is mainly lithium base material.

In embodiments of the invention, the material of diaphragm 3232 is PE (polyethylene) or PP (polypropylene), which can be single layer PE or PP or three layers PE or PP.

Specifically, in the embodiment of the invention, the processing process of battery cavity 323 is as follows:

(1) PET or TPE material is coated inside the upper cover shell 32311 and the lower shell 32312 with a thickness of 300-500 um. It is placed in a constant temperature oven and set the temperature 60-85° C. until the coating material is completely dry;

(2) the battery (comprising cathode plate 3235, diaphragm 3232, anode plate 3234, conductive strip 3237) placed in the lower shell 32312, one end of conductive strip 3237 is fixed on the anode plate 3234 or cathode plate 3235 through solder paste or solder;

(3) The lower shell 32312 is placed in a static position, and the electrolyte 3233 is injected into the lower shell 32312 with a pipette gun, and the whole is moved to the excessive chamber for vacuum standing, to ensure the complete infiltration of the electrolyte, in order to improve the electrochemical performance of the battery cavity;

(4) After the end of the lower shell 32312 standing, the upper cover shell 32311 (circuit board 315) is covered, and the other end of the conductive strip 3237 is fixed on the power electrode 3151 of the circuit board 315 through solder paste or solder, and the sealing joint is coated with sealant to keep the sealing property, and the battery cavity is complete. Sealant is one of hot melt adhesive or silica gel.

To sum up, the present invention discloses a highly integrated analyte detection device, a battery cavity is arranged within the transmitter module, the cavity shell is integrated with the shell of transmitter module. The diaphragm, the electrolyte, the anode plate, the cathode plate and the conductive strip are arranged in the cavity shell, the electrolyte insulation layer is also arranged in the cavity shell, to form the highly integrated analyte detection device with battery, shell of transmitter module and circuit board integration, the shape and size of the analyte detection device are no longer limited by the shape and size of the button battery. After the integration of the battery, shell of transmitter module and circuit board, the battery has more available space and smaller occupied volume, which can meet the design requirements of analyte detection device miniaturization.

Although some specific embodiments of the present invention have been elaborated by examples, those skilled in the field should understand that the above examples are intended only to illustrate and not to limit the scope of the present invention. Those skilled in the field should understand that modifications to the above embodiments may be made without departing from the scope and spirit of the invention. The scope of the invention is limited by the attached claims.

The invention claimed is:

1. A highly integrated analyte detection device, which comprises:

a bottom case used for mounting on a skin surface of a user;

a sensor assembled on the bottom case for detecting analyte parameter information in a body of the user;

a transmitter module comprising a shell, a circuit board, a transmitter and an electrical contact, wherein the electrical contact is electrically connected with the sensor, the transmitter is used to transmit the analyte parameter information to external equipment; and a battery cavity located within the transmitter module, wherein the battery cavity comprises a cavity shell, a diaphragm, electrolyte, an anode plate, a cathode plate and a conductive strip, the cavity shell comprises an upper cover shell and a lower shell, the upper cover shell is integrated with the circuit board, wherein the lower shell and the circuit board jointly accommodate and encompass the diaphragm, the electrolyte, the anode plate, and the cathode plate.

2. The highly integrated analyte detection device according to claim 1, wherein the lower shell is integrated with the shell of the transmitter module.

3. The highly integrated analyte detection device according to claim 1, wherein an electrolyte isolation layer is arranged inside the cavity shell.

4. The highly integrated analyte detection device according to claim 3, wherein the electrolyte isolation layer is made of TPE or PET material.

5. The highly integrated analyte detection device according to claim 4, wherein the electrolyte isolation layer is a film arranged on an inner wall of the cavity shell.

6. The highly integrated analyte detection device according to claim 5, wherein a thickness of the film is 300-500 um.

7. The highly integrated analyte detection device according to claim 4, wherein the electrolyte isolation layer is a closed shell independent of the cavity shell.

8. The highly integrated analyte detection device according to claim 1, wherein the cavity shell material is PE, PP, HDPE, PVC, ABS, PMMA, PC, PPS or PU.

9. The highly integrated analyte detection device according to claim 1, wherein a sealant is coated at a junction of the upper cover shell and the lower shell.

10. The highly integrated analyte detection device according to claim 9, wherein the sealant is one of hot melt adhesive and silica gel.

11. The highly integrated analyte detection device according to claim 1, wherein the anode plate and the cathode plate are electrically connected to the circuit board through the conductive strip.

12. The highly integrated analyte detection device according to claim 11, wherein the conductive strip is fixedly connected to the circuit board by solder or solder paste.

13. The highly integrated analyte detection device according to claim 1, further comprising a connector, which comprises at least two conductive zones and an insulating zone arranged alternately for using as an electrical connection medium for the electrical contact and the sensor.

* * * * *